United States Patent [19]

Hermann

[11] Patent Number: 4,965,344

[45] Date of Patent: Oct. 23, 1990

[54] PROCESS FOR OBTAINING ACTIVE PROTEINS FROM A BIOLOGICALLY INACTIVE FORM

[75] Inventor: Reinhard Hermann, Zoetermeer, Netherlands

[73] Assignee: Behringwerke Aktiengesellschaft, Fed. Rep. of Germany

[21] Appl. No.: 56,721

[22] Filed: Jun. 2, 1987

[30] Foreign Application Priority Data

Jun. 4, 1986 [DE] Fed. Rep. of Germany ....... 3618817

[51] Int. Cl.5 .......................... C07K 3/20; C07K 3/12; C07K 15/26
[52] U.S. Cl. .................... 530/351; 530/412; 530/414; 530/417; 530/422; 530/820; 435/69.1; 435/69.5
[58] Field of Search ............... 530/412, 414, 417, 422, 530/820, 351; 435/803, 814, 68, 69.1, 69.5

[56] References Cited

U.S. PATENT DOCUMENTS

| 3,573,271 | 4/1971 | Nielsen | 530/417 |
| 4,678,553 | 7/1987 | Mandle et al. | 204/182.6 |
| 4,766,205 | 8/1988 | Ghosh-Dastidar | 530/412 |

FOREIGN PATENT DOCUMENTS

| 0114506 | 8/1984 | European Pat. Off. | 435/68 |
| 150066 | 7/1985 | European Pat. Off. | |

OTHER PUBLICATIONS

Knuth et al. 1987. Protein Purification: Micro to Macro. Alan R. Liss, Inc. New York, N.Y.
Scopes, R. *Protein Purification; Principles and Practice*, N.Y. Springer–Verlag, 1982. pp. 151–163.
Hermann et al., The Journal of Biological Chemistry, 258: 11014–11019 (1983).
Good et al., Biochemistry, vol. 5, No. 2 (1966) pp. 467–477.
Jaenicke et al., Methods in Enzymology, vol. 131 pp. 218–250.
Christopherson, Methods in Enymology, vol. 91 pp. 278–281.
Griffith, Journal of Chromatography, vol. 109 (1975) pp. 399–402.
Jaenicke, Angewandte Chemie, vol. 96, (1984) pp. 385–402.

*Primary Examiner*—Margaret Moskowitz
*Assistant Examiner*—Keith C. Furman
*Attorney, Agent, or Firm*—Finnegan, Henderson, Farabow, Garrett and Dunner

[57] ABSTRACT

A process for the preparation of a spatial form, which has biological activity, of a protein from a biologically inactive spatial form is described and comprises the protein being dissolved with the addition of a denaturing agent and thus converted into the random coil form, and the solution being allowed to pass through a material which has molecular sieve properties and contains a liquid medium in which the protein can assume a spatial form which has biological activity, and this material having molecular sieve properties being selected so that the molecules of the denaturing agent can penetrate, but the protein molecules canot. It is possible by centrifugation, blowing or sucking out to remove the medium in the "external volume" of the molecular sieve and to increase the rate of passage of the solution through the molecular sieve.

15 Claims, 4 Drawing Sheets

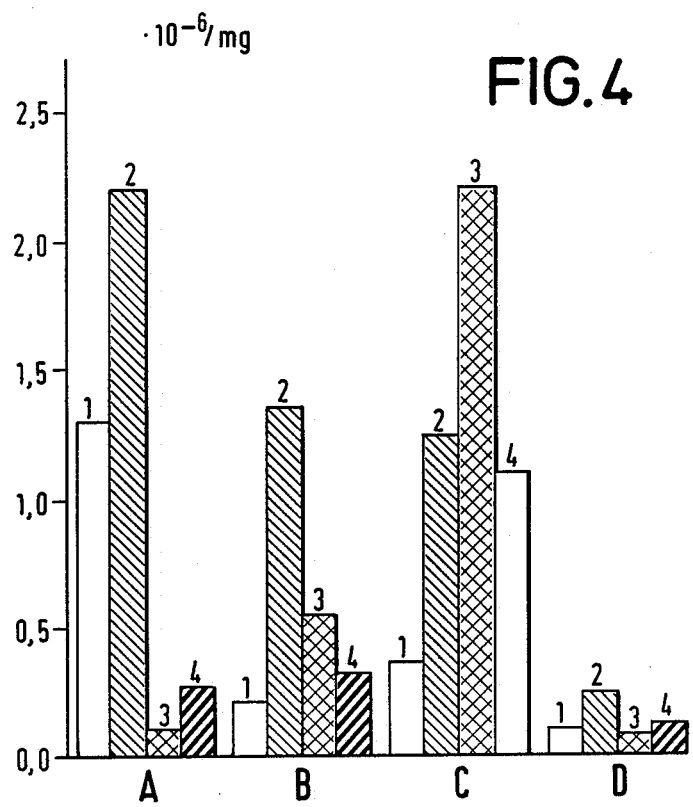

PROCESS FOR OBTAINING ACTIVE PROTEINS FROM A BIOLOGICALLY INACTIVE FORM

The invention relates to a process for converting a protein from a conformation in which it is biologically inactive into a biologically active form. In the case of a denatured natural protein it would also be possible to call this process renaturation.

BACKGROUND OF THE INVENTION

Purification and sterilization processes applied to protein preparations may result in partial denaturation of the protein employed. Hitherto it was preferable, particularly based on economic considerations, to separate out and discard denatured protein. Protein prepared by gene manipulation in prokaryotes is largely in a biologically inactive form.

In order to raise the yield of "natural" protein, that is to say that with the correct spatial structure and the biological activity of the natural protein, it is necessary first for the polypeptide chain to be unfolded to give a random coil, and any incorrect disulfide bridges which are present to be reduced. This is normally carried out by incubation in at least 4 mol/l guanidine hydrochloride solution or at least 6 mol/l urea solution, where appropriate with the addition of a reducing agent such as dithiothreitol (DTT). Subsequently, the formation of the correct protein structure has, to date, been brought about by dilution (at least 1:40) or dialysis against a "physiological" buffer solution.

It is hardly possible to use either method industrially. Dilution of volumes which are large at the outset, followed by reconcentration, is time-consuming, troublesome and costly. This is similarly true of dialysis of large volumes. Furthermore, slow removal of denaturing agent considerably reduces the reactivation yield because side-reactions, such as aggregations, take place preferentially in the intermediate range of concentrations of denaturing agent.

SUMMARY OF THE INVENTION

It has been found, surprisingly, that the disadvantages of the processes of the prior art can be avoided by removing the denaturing agent from the solution containing the denaturing agent and the protein by allowing the solution to pass through a material which has molecular sieve properties and which contains a medium in which the protein assumes its biologically active form, the selected pore size of this molecular sieve material being such that the denaturing agent can penetrate, but the protein cannot.

Thus the invention relates to a process for the preparation of a spatial form, which has biological activity, of a protein from a spatial form which is biologically inactive, which comprises the protein being dissolved with the addition of a denaturing agent and thus converted into the random coil form, and the solution being allowed to pass through a material which has molecular sieve properties and contains a liquid medium in which the protein can assume its spatial form which has biological activity, and this material having molecular sieve properties being selected so that the molecules of the denaturing agent can penetrate, but the protein molecules cannot.

BRIEF DESCRIPTION OF THE DRAWINGS

FIG. 4 is a bar diagram showing results obtained in Example 4.

DESCRIPTION OF PREFERRED EMBODIMENTS

Figure 1:
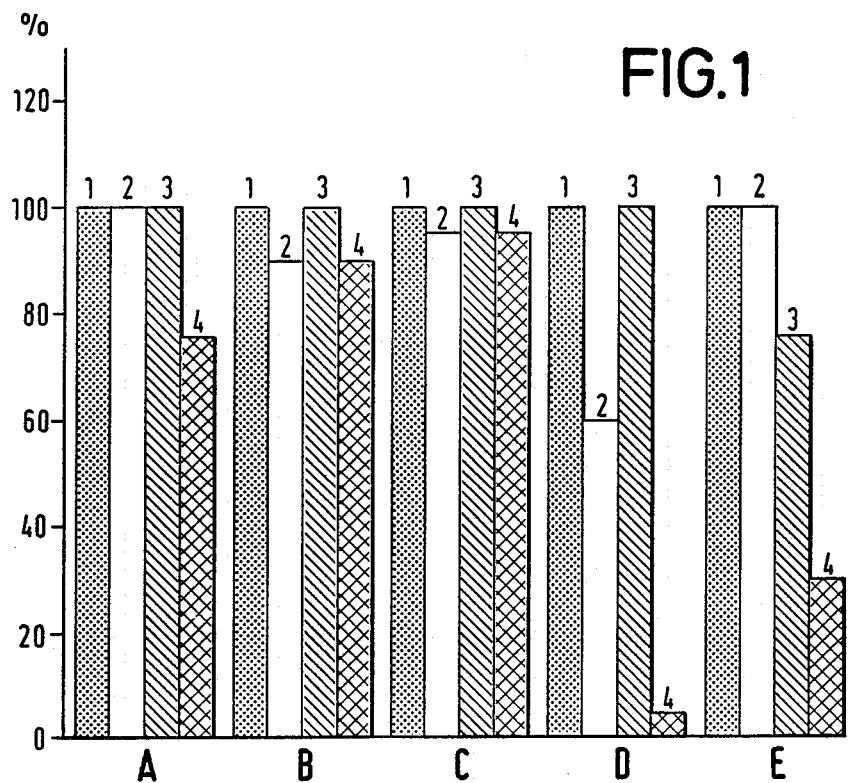
FIG. 1 is a bar diagram showing results obtained in Example 1.

Examples of possible locations of the molecular sieve are a column or a centrifuge basket.

Once the molecular sieve has been equilibrated with the medium in which the protein can assume a biologically active form it is preferable for the portion of the medium which is not located in the pores of the molecular sieve (the "external volume") to be removed. This is expediently achieved by centrifugation, but can also be brought about by, for example, blowing out with a gas or sucking out by applying a vacuum.

The solution which contains the "unfolded" protein and the denaturing agent is then applied to the molecular sieve. The penetration of the solution through the molecular sieve material should be effected by a force exceeding the force of gravity. Centrifugation is preferred for this, but it is also effected by gas pressure or vacuum. When centrifugation is employed the operating procedure substantially corresponds to the known techniques of basket or screen centrifugation.

A molecular sieve of this type may be one of the materials which are known for gel filtration and which is chemically resistant to the denaturing agent, for example SEPHADEX G-25, DG 6P (BIO RAD, USA) or controlled pore glass. The pore size is selected so that the denaturing agent can penetrate into the matrix, but the protein cannot. The exclusion limit will usually be at a Mr of 6,000 to 10,000 (Mr=molecular weight).

It is equilibrated with a solution in which the protein assumes its active form, preferably with a buffer, and transferred, for example, into a column, which can preferably be centrifuged, or into a centrifuge basket. The solution not located in the pores of the matrix (not "in the internal volume") is preferably removed by centrifugation at about 300–1,000×g. The protein solution containing the denaturing agent is then applied (volume less than 30% of the gel volume). Whereas molecules of the denaturing solution can replace the buffer in the internal volume, proteins (molecular weight above 6,000) remain in the external volume. It is possible by renewed centrifugation (2 min, 300–1,000×g) to spin the proteins quantitatively into a collecting vessel. This can be carried out by centrifugation in a basket centrifuge in accordance with known desalination processes. No denaturing agents are detectable thereafter. The volume of the resulting solution then corresponds to the volume of the solution applied.

The removal of the equilibration medium in the external volume, as well as the speeding up of the replacement of the equilibration medium in the internal volume by the denaturing agent contained in the protein solution, can also be brought about by gas pressure or vacuum.

The process according to the invention makes it possible to transfer, rapidly, quantitatively and without dilution, a protein even from large volumes of a denaturing medium into a medium in which the protein assumes an active form, and to obtain high yields of active protein.

It is possible in the manner described for protein material which cannot otherwise be exploited to be rendered commercially utilizable.

The process is distinguished by simplicity, rapidity and reproducibility. It is possible to carry it out using available and conventional equipment and materials. After use, the gel material can be regenerated and, for example, guanidine hydrochloride can be recovered. The protein concentration remains unchanged.

Denatured proteins are, specifically, proteins in an unnatural state after a heat treatment, for example for inactivation of infectious material, after acid treatment, for example acid cleavage of fusion proteins obtained by gene manipulation, after treatment with structure-damaging agents, for example during the course of purification, extraction or solubilization steps and on inactivation of infectious material, or after preparation by gene manipulation resulting in an incorrect conformation and/or incorrect formation of disulfide bridges.

Examples of suitable denaturing agents for complete unfolding of the protein are high-molarity solutions of guanidinium salts, urea or other chaotropic molecules, where appropriate in the presence of a reducing agent, for example 50–150 mmol/l dithiothreitol (DTT). Examples of the usual concentrations are for guanidine salts 4–7, for urea 6–8 and for isothiocyanate 6–8 mol/l and for 2-chloroethanol about 400 ml/l.

The development of the biologically active (natural) structure is brought about by rapid transfer into a buffer which favors the natural structure.

The rapidity of the transfer is important for a high yield. In the process described, the time is in the range of seconds to minutes.

Examples of suitable activating buffers are phosphate or tris buffer or buffers known as "Good buffers" (Biochem. (1966) 15, 467–477) which are adjusted to the pH of maximum activity or stability of the protein.

The denaturing molecules are rapidly and quantitatively removed, preferably by centrifugation.

The medium in which the protein assumes its biologically active conformation is usually a buffer and has a composition which is advantageous for the stability of the protein (contains, for example, phosphates, sulfates, citrates). Examples of other additives it can contain are sugars, peptides or proteins to stabilize the natural structure, or detergents, for example TWEEN 20 or NP40 to prevent adhesion or aggregation and/or for solvation, and/or SH reagents or redox systems, for example DTT or glutathione/glutathione disulfide (GSH/GSSG) to set up the redox potential which is optimal for the formation of correct disulfide bridges.

Reproducible redox conditions are ensured by degassing the buffers and saturating with nitrogen.

Basket centrifugation within the meaning of the invention is every centrifugation technique in every volume range with any equipment, in which any desired macromolecule (in buffer A) is transferred by centrifugation through a gel filtration medium, which has been equilibrated with buffer B and optionally precentrifuged, into buffer B.

The examples which follow illustrate the invention.

EXAMPLE 1

Denaturation of active mouse GM colony stimulating factor (Mu GM-CSF, recombinant from yeast) in guanidine, and reactivation.

3 samples, each comprising 1 μg, of each of 5 solutions of GM-CSF of 5 different degrees of glycosylation (A to E) were taken up in 40 pl of 6 mol/l guanidine.HCl in phosphate-buffered saline (PBS), pH 7.2, and the solution was kept at room temperature for 60 minutes.

A SEPHADEX G-25 molecular sieve was packed into 15 tubes with a volume of 0.5 ml, and groups of 5 were equilibrated with degassed, nitrogen-saturated PBS containing no additive or containing 1 mmol/l DTT or 0.02 ml/100 ml TWEEN detergent. The liquid in the external volume was spun out at $700 \times g$ (5 minutes). In each case, one of the 5 solutions of GM-CSF (A to E) was applied to one of these 5 tubes equilibrated with PBS or with PBS+DTT or TWEEN detergent.

Immediately after the 15 different solutions had been applied to the 15 tubes they were centrifuged at $700 \times g$ for two minutes and 15 samples of 40 μl of a guanidine-free GM-CSF preparation were obtained.

All 15 samples were stored overnight at room temperature under nitrogen, and then the activity was determined in the bone marrow test or on a GM-CSF-dependent cell line.

The activity of the guanidine-treated samples depended on the reactivation buffer and ranged up to 100% of the initial activity (about $2 \times 10^7$ units (U)/mg). The yield of protein, determined by SDS electrophoresis and Western blot, was virtually quantitative.

The results are shown in FIG. 1. In this diagram, in each case 1 designates the column for the activity of the solution of GM-CSF which has not been treated with denaturing agent and reactivated, and 2 designates that for the GM-CSF reactivated in PBS, 3 that in PBS and ®Tween, and 4 that in PBS and DTT. A to E each designate one group of activities for one of five GM-CSF preparations with differing extents of glycosylation.

EXAMPLE 2

Unfolding in 6 mol/l guanidine and activation of aggregated recombinant human GM-CSF.

2 preparations of aggregated, freeze-dried human GM-CSF (A and B), which had been obtained by acid cleavage of a fusion protein from E. coli, were each dissolved in 6 mol/l guanidine.HCl in PBS and incubated at room temperature for 60 minutes. The CSF contribution to the total protein was about 20 micrograms/100 micrograms.

Subsequent treatment was carried out as in Example 1.

Figure 2:
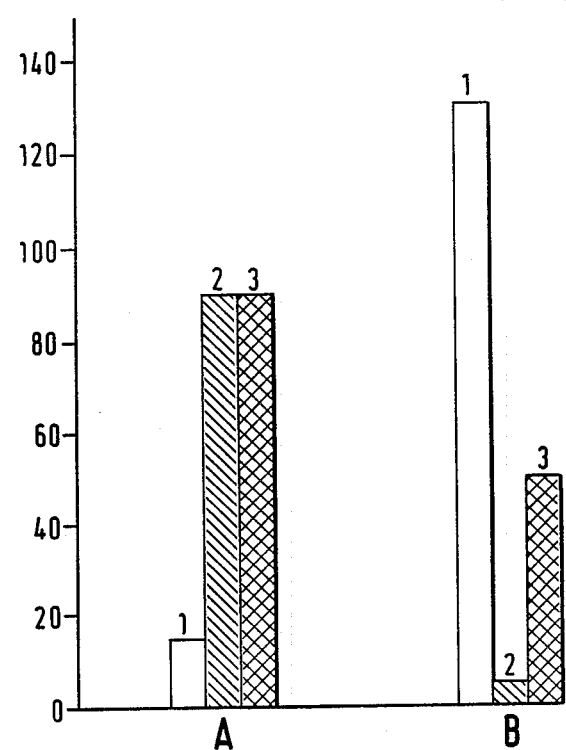
FIG. 2 is a bar diagram showing results obtained in Example 2.

The results are shown in FIG. 2.

The activity of the guanidine-treated samples reached an activity which was up to 130 times the initial activity. The maximum specific activity was determined to be $2 \times 10^7$ units/mg. The reactivation buffers used were PBS (columns No. 1), PBS+0.02% TWEEN 20 detergent (columns No. 2) or PBS +0.1 mmol/l dithiothreitol (columns No. 3).

EXAMPLE 3

Figure 3:
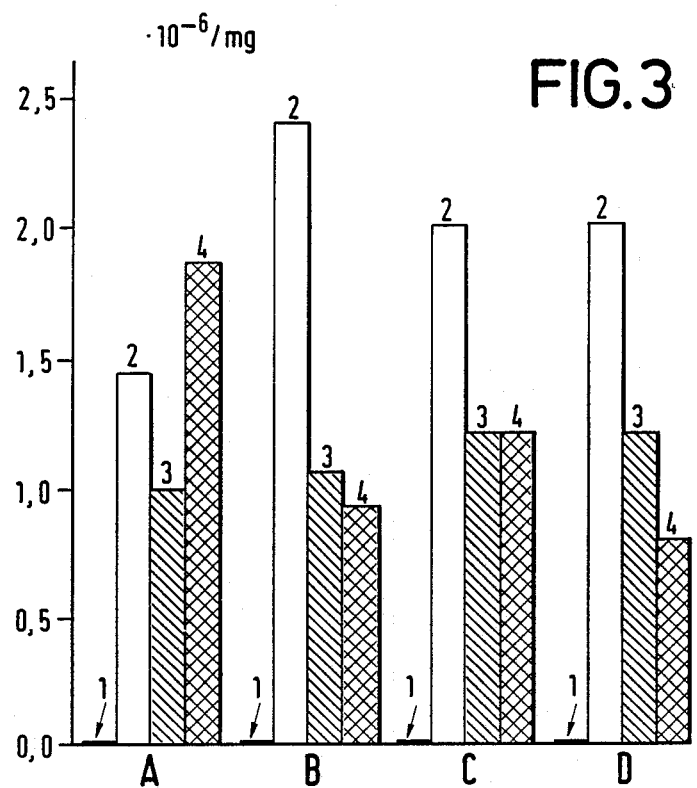
FIG. 3 is a bar diagram showing results obtained in Example 3.

Unfolding in 8 mol/l urea and activation of aggregated, inactive recombinant human GM-CSF Aggregated, freeze-dried human GM-CSF from *E. coli* (3 samples after acid cleavage designated A, B and C, and one sample which was not cleaved and was designated D;

CSF content about 20 μg/100 pg of total protein) was dissolved in 8 mol/l urea in tris.HCl, pH 8.0 (protein concentration 1 mg/ml, volume of each sample 0.5 ml) and incubated at room temperature for 60 min. The subsequent treatment was carried out as in Example 1. The reactivation buffer used was PBS (columns No. 1) or PBS+0.02% Tween (columns No. 2), PBS+"low"* GSH (columns No. 4) or PBS+"high"* GSH (columns No. 3) after acid cleavage. In all cases specific activity near to or the same as the maximum specific activity was obtained from completely inactive material (FIG. 3).

* "low" GSH: 25 μM GSH/50 μM GSSG (corresponds to the extracellular redox potential)
* "high" GSH: 5 mM GSH/0.1 mM GSSG (corresponds to the intracellular redox potential)

Fusion protein before cleavage also shows considerable biological activity (D). The specific activity after reactivation was determined to be $1-2\times 10^7$ units/mg.

EXAMPLE 4

Unfolding and complete reduction of all the disulfide bridges in aggregated, inactive, recombinant human GM-CSF, refolding and reoxidation to give the biologically active material as in Example 3.

Denaturation and reduction in 8 mol/l urea in tris.HCl of pH 8.0+0.15 mol/l dithiothreitol; folding to give the biologically active product in PBS (columns No. 1) or PBS+0.1% human serum albumin (columns No. 2), PBS+high GSH (columns No. 3) or PBS+low GSH (columns No. 4) (FIG. 4).

I claim:

1. A process for converting proteins to an active conformation from a biologically inactive conformation comprising:

treating a protein with a denaturant that solubilizes the protein and converts the protein into a denatured, random coil biologically inactive conformation;

applying the denatured protein and the denaturant solution to a sieve material having molecular sieve properties, said sieve material having an internal volume including pore means and an external surface area outside the internal volume, said pore means being dimensioned such that protein molecules are prevented from penetrating into the internal volume and such that the denaturant can enter the internal volume, said sieve material being preequilibrated with an appropriate renaturation buffer and said renaturation buffer being removed from the external surface are by mechanical force prior to the application of the denatured protein and the denaturant; and applying a force exceeding the force of gravity to the denatured protein and the denaturant solution such that the solution passes through the sieve material without the protein entering the pore means of the sieve material, thereby substantially replacing the denaturant solution with the renaturation buffer, and thereby forcing the protein and renaturation buffer out of the sieve material to obtain protein in an active conformation.

2. The process as in claim 1, wherein the material having molecular sieve properties is selected from the group consisting of SEPHADEX G-25, molecular sieve BIO RAD DG 69 molecular sieve and controlled pore glass.

3. The process as claimed in claim 1, wherein the renaturation buffer in which the protein assumes a biologically active form is an aqueous buffer which contains agents favorable to the activity and stability of the protein selected from the group consisting of buffers adjusted to the pH of maximum activity or stability of the protein, stabilizers, detergents, disulfide reagents, redox systems and wetting agents.

4. The process as claimed in claim 1, wherein the step of applying force to the denatured protein and the denaturant solution includes applying centrifugal force.

5. The process as claimed in claim 1, wherein the step of applying the denatured protein and the denaturant solution to the sieve material includes using gel filtration material as the sieve material.

6. The process as claimed in claim 1, wherein the step of treating the protein with a denaturant comprises using a denaturant solution which includes a disulfide reducing agent.

7. The process as claimed in claim 1, wherein the step of treating the protein with a denaturant comprises using a denaturant solution which comprises about 6M to about 8M urea or about 4M to about 7M guanidine-HCl.

8. The process as claimed in claim 1, wherein the protein has a concentration of about 25 μg/ml to about 1 mg/ml prior to the converting of the protein to the active conformation.

9. The process as claimed in claim 1, wherein the protein is human granulocyte macrophage colony stimulating factor and the human granulocyte macrophage colony stimulating factor in the active conformation is obtained with about 100% of the activity present before treating the protein with the denaturant.

10. The process as claimed in claim 1, wherein the protein is recombinant human granulocyte macrophage colony stimulating factor and the recombinant human GM-CSF obtained in the active conformation has activity substantially indistinguishable from natural human granulocyte macrophage colony stimulating factor activity.

11. The process as claimed in claim 1, wherein the step of removing the renaturation buffer from the external surface area by mechanical force comprises using at least one member of the group consisting of suction, centrifugation and gas pressure.

12. The process as claimed in claim 1, wherein the step of applying force to the denatured protein and the denaturant solution includes applying at least one member of the group consisting of suction and gas pressure.

13. The process as claimed in claim 1, wherein the protein obtained in the active conformation is substantially free of denaturant.

14. The process as claimed in claim 1, wherein the step of applying force to the denatured protein and the denaturant solution consists essentially of applying centrifugal force.

15. The process as claimed in claim 1, wherein the protein is human granulocyte macrophage colony stimulating factor and the human granulocyte macrophage colony stimulating factor in the active conformation is obtained in a yield of about 100%.

* * * * *

UNITED STATES PATENT AND TRADEMARK OFFICE
CERTIFICATE OF CORRECTION

PATENT NO. : 4,965,344
DATED : October 23, 1990
INVENTOR(S) : Reinhard Hermann

It is certified that error appears in the above-identified patent and that said Letters Patent is hereby corrected as shown below:

Title Page:

<u>In the Abstract</u>

Line 12, "canot" should be --cannot--;

Claim 1, Column 5, Line 54, "are" should be --area--;

Claim 2, Column 6, Line 1, "G-25, molecular sieve" should be --G-25 molecular sieve,--.

Signed and Sealed this

Twentieth Day of October, 1992

Attest:

DOUGLAS B. COMER

*Attesting Officer*   *Acting Commissioner of Patents and Trademarks*